United States Patent [19]

Borel

[11] 4,292,234

[45] Sep. 29, 1981

[54] SILANE REINFORCING PROMOTERS IN REINFORCEMENT OF SILICA-FILLED RUBBERS

[75] Inventor: Albert W. Borel, Jennings, La.

[73] Assignee: Phillips Petroleum Co., Bartlesville, Okla.

[21] Appl. No.: 25,508

[22] Filed: Mar. 30, 1979

[51] Int. Cl.$^3$ ............................................... C08K 9/06
[52] U.S. Cl. ................................ 260/42.15; 260/762; 260/349; 556/406; 556/413; 556/427
[58] Field of Search ............. 260/42.15, 762, 448.2 N, 260/448.8 R

[56] References Cited

U.S. PATENT DOCUMENTS

| | | | |
|---|---|---|---|
| 3,655,713 | 4/1972 | Le Grow | 260/448.2 N |
| 3,697,551 | 10/1972 | Thomson | 260/349 |
| 3,813,351 | 5/1974 | Thomson | |
| 3,947,436 | 3/1976 | Rocktaschel et al. | 260/42.15 |
| 3,957,718 | 5/1976 | Pochert et al. | 260/42.15 |
| 4,143,027 | 3/1979 | Sollman et al. | 260/42.15 |

FOREIGN PATENT DOCUMENTS 2704506  8/1977  Fed. Rep. of Germany.
1377214 12/1974  United Kingdom.

Primary Examiner—Lewis T. Jacobs

[57] ABSTRACT

At least one of an alkoxy alkyl substituted silylazide, an alkoxy alkyl substituted silyl thiosulfenamide, a silacycloalkyl mercaptan and/or a bis(silacycloalkyl) disulfide is employed as a coupling agent or promoter in a silica-filled rubber.

The mentioned compounds are novel.

16 Claims, No Drawings

SILANE REINFORCING PROMOTERS IN REINFORCEMENT OF SILICA-FILLED RUBBERS

This invention relates to certain novel compounds which can be broadly termed to the azides, mercaptans, and disulfides. The invention also relates to the use of certain azides, mercaptans, disulfides and thiosulfenamides as coupling agents or promoters in the production of silica filled rubber compositions.

In one of its concepts, the invention provides, broadly described, as a novel compound or compound, useful as coupling agent or promoter as further described therein an alkoxy alkyl substituted silyl thiosulfenamide, an alkoxy alkyl substituted silyl azide, a silacycloalkyl mercaptan and a bis(silacycloalkyl) disulfide. In a more specific concept of the invention there is provided certain recited specific compounds as herein formulated and set forth.

In another concept of the invention, it provides the production of a silica filled rubber composition comprising as a coupling agent or promoter therein at least one of the compounds recited herein and identified as suitable for use as a coupling agent or promoter in the process of the invention also as described herein.

A major reinforcing agent for rubber-based products such as tires and extruded and molded goods is carbon black. Carbon black greatly enhances mechanical strength and resistance to abrasion and is thus widely used which explains why the annual worldwide production of carbon black is over 2 billion pounds. Carbon black is produced by the thermal decomposition of hydrocarbons principally oil and natural gas. The increasing demand for other oil or gasderived petrochemicals plus the decreasing supply of oil and natural gas has prompted searches for a carbon black replacement.

The best nonblack reinforcing pigments so-far developed are the reinforcing silicas which come the closest to carbon black properties of any available material. Cost has heretofore eliminated the use of silica as a serious competitor to carbon black. However, with the advent of new processes some amorphous and fine particle-size silica have emerged which are considered to be economically competitive to carbon black. In addition, promoters or coupling agents have greatly increased the performance level of silica as a rubber reinforcing filler. While full equivalence with carbon black has not yet been achieved, the possibility still exists that better promoters might make silica competitive with carbon black on a performance basis, hence, the need exists for better promoters or coupling agents for silica reinforcing agents.

It is an object of this invention to provide at least one novel compound. It is another object of this invention to provide at least one novel compound suitable for use as a promoter or coupling agent in the compounding of silica filled rubber compositions. It is another object of this invention to provide a method for the improved compounding of a silica filled rubber. A further object of the invention is to provide novel silica filled rubbers having improved properties.

Other aspects, concepts, objects and several advantages of the invention are apparent from a study of this disclosure and the appended claims.

According to the present invention there is provided a compound suitable for use as a coupling agent in the silica filler reinforcement of a rubber, said compound being represented by one of the following formulas.

$$(RO)_{3-n}R'_nSi(CH_2)_xY \quad (I)$$

wherein R and R' are at least one of a linear or branched alkyl or cycloalkyl group having from one to ten carbon atoms and aromatic or substituted aromatic groups having from six to ten carbon atoms, x is an integer from 1 to 20 and Y is an azide, and

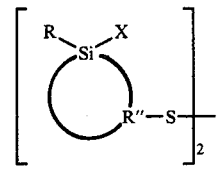 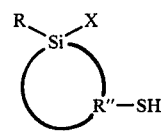

(II)        (III)

wherein X is at least one of a halogen and an alkoxy (-OR) group where R in said group and in said formulas A and B is as previously defined and R'' is a trivalent hydrocarbon radical having 2 to 10 carbon atoms.

Also according to the present invention there is provided a process or method for the improved compounding of a silica filled rubber composition employing as coupling agent or promoter at least one of a compound as already defined and as exemplified later herein and an alkoxy substituted silyl alkyl thiosulfenamide in which the substituted thiosulfenamide group can be represented by the formula

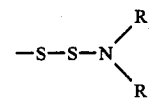

wherein each R is the same or different and are as defined herein.

The following are examples of the azide derivatives of this invention.
trimethoxysilylmethylazide,
2-(trimethoxysilyl)ethylazide,
3-(trimethoxysilyl)propylazide,
4-(trimethoxysilyl)butylazide,
3-(triethoxysilyl)propylazide,
4-(triethoxysilyl)butylazide,
etc., and the dimers, trimers, thereof etc. of the azide derivatives herein described are also useful in this invention.

Representative, but not limited to, are the following examples of the silacyclic compounds of this invention corresponding to formula II.
bis(1-chloro-1-methyl-1-sila-3-cyclopentyl) disulfide,
bis(1-chloro-1-ethyl-1-sila-3-cyclopentyl) disulfide,
bis(1-ethoxy-1-methyl-1-sila-3-cyclopentyl) disulfide,
bis(1-ethoxy-1-ethyl-1-sila-3-cyclopentyl) disulfide,
bis(1-chloro-1-methyl-1-sila-3-cyclohexyl) disulfide,
bis(1-chloro-1-methyl-1-sila-4-cyclohexyl) disulfide,
bis(1-methoxy-1-ethyl-1-sila-4-cyclohexyl)disulfide, disulfide,
bis(1-butoxy-1-butyl-1-sila-4-cyclohexyl) disulfide,
etc., and mixtures thereof.

Representative, but not limited to, are the following examples of the compounds of Formula III.
1-chloro-1-methyl-3-mercaptosilacyclopentane
1-bromo-1-ethyl-3-mercaptosilacyclopentane 1-chloro-1-methyl-4-mercaptosilacyclohexane
1-ethoxy-1-methyl-3-mercaptosilacyclopentane
1-methoxy-1-ethyl-4-mercaptosilacyclohexane
1-butoxy-1-butyl-4-mercaptosilacyclohexane
etc., and mixtures thereof.

The following are examples of the thiosulfenamide derivatives of this invention:
N,N-dimethyl(trimethoxysilyl)methylthiosulfenamide,
N,N-dimethyl-2-(trimethoxysilyl)ethylthiosulfenamide,
N,N-dimethyl-3-(trimethoxysilyl)propylthiosulfenamide,
N,N-diethyl-3-(triethoxysilyl)propylthiosulfenamide,
etc., and mixtures thereof.

The amount of promoter or coupling agent used in this invention can be broadly from 0.05 to 10 phr (parts of coupling agent per hundred parts of rubber employed). It is preferred to use 0.1 to 3.0 phr.

One or more of the coupling agents herein disclosed can be used together. Use of the term "promoter" and/or the term "coupling agent" is not to be taken as limiting the action of the additive(s) of the invention claimed.

The elastomer or rubber component of this invention can be any type although it is preferred that the rubber be subject to a sulfur type vulcanization and as such should have some degree of unsaturation. Typical elastomers useful in this invention are for example: natural rubber, homopolymers of conjugated dienes such as butadiene and isoprene, copolymers of conjugated dienes and vinyl aromatics which would include SBR and solution polymerized rubbers, butyl rubber, and nitrile rubber. The polymers can be linear or branched.

Any type silica can be employed which is considered to have reinforcing properties. Generally this will be silicas with a particle size less than 15 microns and an external surface area of 50 to 250 meters per gram with low porosity (i.e. <20 square meters per gram). Generally, precipitated grade silica is preferred over fumed grade silica because of the difference in cost of preparation. Typical examples of some commercial silicas useful in this invention are Hi Sil 233 (PPG Industries), Aerosil (Degussa) and Cabosil (Cabot Corp.).

The recipe used in this invention is considered to be conventional (see U.S. Pat. No. 3,798,196, Examples V to VIII) and thus not critical to the successful operation of the invention, the important feature being the selection of the promoter. The recipe used is shown in Table I.

TABLE I

| Ingredients - Parts | | Standard Formulation Identity of Ingredient |
| --- | --- | --- |
| SBR 1500 | 100 | Emulsion Rubber. 76.5 wt. % butadiene/23.5 wt. % styrene copolymers |
| Hi Sil 233 | 40 | Precipitated hydrated silica, 0.022 micron (PPG Industries) |
| Stearic acid | 2 | — |
| Zinc oxide | 4 | — |
| Altax | 1.5 | Accelerator-Benzothiazyl disulfide (R. T. Vanderbilt) |
| DPG | 1.5 | Accelerator-Diphenyl guanidine |
| Sulfur | 2.75 | — |
| Coupling Agent | 0 to 1.5 | Variable as shown |

Variations in the quantity of the ingredients or even in the selection of other type ingredients is left to the discretion of those skilled in the art. Likewise, mixing of the ingredients in any suitable mixer and curing or vulcanizing of the formulation is also left to the needs and know-how of those skilled in the art. The recipe shown in Table I was mixed on a 5.08 cm (2 inch) lab rubber mill for 19 mins. The recipe was cured 30 mins at 160 C.

The following examples serve to illustrate the preparation of the inventive compounds and their usefulness as coupling agents in silica-filled sulfur vulcanized rubber compositions.

EXAMPLE I

3-(Trimethoxysilyl)propylazide and Dimer

To a 2 liter, 3-necked round bottom glass flask fitted with a stirrer, heating mantle, reflux condenser, and nitrogen inlet source was charged 99 grams (0.5 mole) of a 3-trimethoxysilylpropylchloride, 112 grams (1.72 moles) sodium azide and 1 liter of methanol. The mixture was stirred at reflux temperature for 11 days, cooled to about 10 C. in a wet-ice bath and filtered. The filtrate was concentrated under vacuum on a steam bath. The semi-solid sludge was treated with 0.2 liter n-heptane, filtered and again concentrated under vacuum on a warm water bath. Continued distillation gave a 62 mole % yield of product (74 C./63 mm) comprised of 92 wt.% azide product and 8 wt.% 3-trimethoxysilylpropylchloride.

The kettle product from the above distillation was analyzed by gas-liquid chromatography and found to contain 40 wt.% 3-(trimethoxysilyl)propylazide, 62 wt.% dimer of 3-(trimethoxysilyl)propylazide and 34 wt.% unknowns.

EXAMPLE II

N,N-Diethyl-3-(trimethoxysilyl)propylthiosulfenamide

To a 3 liter 3-necked round bottom glass flask fitted with a dry-ice/acetone condenser, stirrer and dropping funnel was charged 196 grams (1.0 moles) 1-mercapto-3-trimethoxysilylpropane and 2 liters of n-pentane. The mixture was stirred until completely homogeneous afterwhich 135 grams (1.0 moles) of sulfuryl chloride was slowly added with stirring at room temperature. Nitrogen was slowly passed through the mixture for about 20 minutes. The liquid contents were transferred to a dropping funnel and slowly added at about 25 C. to a stirred solution of 160 grams (2.19 moles) diethylamine and 0.3 liter n-pentane. After the addition was complete (2 hrs) the mixture was stirred for an additional 0.5 hrs., filtered and the solid residue washed with 0.5 liters n-pentane. The n-pentane solvent was removed under vacuum with nitrogen. Nitrogen was passed through the residue for 16–20 additional hours under atmospheric conditions. The remaining sludge was again filtered to give 204 grams (68 mole % yield) of a liquid product considered to be the desired product. Analysis by GLC indicate 64.13% purity. Elemental analysis based on 64.13% pure $C_{10}H_{25}O_3NS_2Si$ is: Calc. N, 2.99; S, 13.7. Found N, 3.97; S, 12.9.

EXAMPLE III

1-Chloro-1-Methyl-3-Mercaptosilacyclopentane

To a 0.5 liter concentric quartz glass tube ultraviolet light reactor mounted on a horizontal shaker and equipped with a thermowell, an internal cooling coil, a 100-watt mercury vapor lamp, and a sampling valve was charged 145.8 grams (1.09 moles) 1-chloro-1-methylsilacyclopentene-2 (CMSCP), 0.003 liters trimethylphosphite, 0.0015 liters propylene oxide and 187 grams (5.5 moles) hydrogen sulfide. The reactor was mechanically shaken at 60 cycles per minute while the contents were irradiated for 8.5 hours after which excess hydrogen sulfide was vented off and the remaining contents distilled in pressence of 0.3 grams elemental sulfur, the sulfur being added to prevent reaction between the mercaptan product and any unreacted CMSCP during distillation. The desired product distilled at 76° C./10 mm to give 113.8 grams (61.9 mole % yield) with 98.2 wt.% purity.

EXAMPLE IV

Bis(1-Chloro-1-Methyl-1-Sila-3-Cyclopentyl) Disulfide

To a 0.5 liter 3-neck round bottom glass flask fitted with a magnetic stirrer, dropping funnel and a nitrogen source was added 33.4 grams (0.20 moles) of 1-chloro-1-methyl-3-mercaptosilacyclopentane and 0.025 liters of n-heptane. Sulfuryl chloride, 13.5 grams (0.10 moles) was rapidly added at 25 C. to the stirred mixture within 3 minutes. After an additional stirring for 42 hours at ambient room temperature, the solvent was removed at about 50 -75 C./20-50 mm and nitrogen bubbled through the viscous residue for 16-20 hours. GLC analysis of the residue (27 grams) indicated 90.2 wt.% of the desired disulfide and 9.8 wt.% of the mercaptan starting material. Based on the purity of the residue, a 74 mole % yield was obtained.

EXAMPLE V

1-Ethoxy-1-Methyl-3-Mercaptosilacyclopentane

To a 0.5 liter 3-neck round-bottom glass flask was charged 16.7 grams (0.10 moles) of 1-chloro-1-methyl-3-mercaptosilacyclopentane and 0.225 liters of ethanol and 10 grams of triethylamine. The mixture was stirred and refluxed for 16-20 hours. The solvent was removed at 50-75 C./10-50 mm and nitrogen bubbled through the liquid residue at 25 C. for an additional 16-20 hours. After standing for two more days at about 25° C., the mixture was filtered to give 12.4 grams of a liquid product analyzed by GLC to be about 93% pure. Based on these analysis, a 65.5 mole % yield was obtained.

EXAMPLE VI

The following recipe was used with the various coupling agents:

|  | Parts |
|---|---|
| SBR 1500 | 100 |
| Silica (Hi Sil 233) | 40 |
| Stearic acid | 2 |
| Zinc oxide | 4 |
| Benzothiazyl disulfide | 1.5 |
| Diphenyl guanidine | 1.5 |
| Sulfur | 2.75 |
| Coupling agent | 1.5 |

Compounds were mixed in a 0.4× batch size on a 5.08 cm (2.0 inch) laboratory rubber mill, using the following milling schedule:

|  | Time, mins |
|---|---|
| Breakdown | 2 |
| Filler addition | 5 |
| Promoter addition | 2 |
| Curative addition | 2 |
| Cut and fold | 2 |
| Fold and tight pass | 3 |
| Remill | 3 |

Vulcanization time was 30 min. at 160° C.

Using the procedure of this example, a rubber composition was prepared employing a known silicon-based coupling agent, bis(3-triethoxysilylpropyl) tetrasulfide. In addition, three commercially available alkoxy alkyl silanes were also evaluated for comparative purpose. These results listed in Table II are used as controls for the silyl compounds of this invention. With exception of the known coupling agent, Si 69 (No. 2, Table II), all of the remaining commercial alkoxysilanes (Nos. 3,4,5; Table II) were considered unsatisfactory either because of low strength (300% modulus) or low scorch time.

TABLE II

Performance Properties of Rubber Compositions Employing Various Commercial Silicon-Based Coupling Agents

| No. | Coupling Agent (1.5 phr) Name | Structure | 300% Modulus[a] MPa | psi | Tensile Strength[a] MPa | psi | % Elongation | ΔT, °C.[b] | Dispersion Rating[c] | Scorch Time[d], mins |
|---|---|---|---|---|---|---|---|---|---|---|
| 1. | Control-No coupling agent | — | 5.48 | 795 | 20.4 | 2954 | 654 | 35.2 | 8 | 17.85 |
| 2. | Bis(3-triethoxysilyl-propyl) tetrasulfide[e] | [(C$_2$H$_5$O)$_3$Si(CH$_2$)$_3$—S—S]$_2$ | 13.98 | 2028 | 22.6 | 3278 | 446 | 27.7 | 8 | 12.55 |
| 3. | 3-(Triethoxysilyl)propylamine[f] | (C$_2$H$_5$O)$_3$Si(CH$_2$)$_3$—NH$_2$ | 6.46 | 937 | 15.9 | 2316 | 518 | 30.8 | 9 | — |
| 4. | 3-(Trimethoxysilyl)propylchloride[g] | (CH$_3$O)$_3$Si(CH$_2$)$_3$—Cl | 7.28 | 1056 | 22.1 | 3200 | 618 | 30.9 | 9 | — |
| 5. | 3-(Trimethoxysilyl)propylmercaptan[h] | (CH$_3$O)$_3$Si(CH$_2$)$_3$—SH | 19.28 | 2796 | 30.3 | 4389 | 445 | 24.8 | 8 | 3.6 |

[a]Determined according to ASTM D-412-75
[b]Determined according to ASTM D-623-62. Also referred to as hysteresis.
[c]Determined similar to ASTM D-26-63. Samples cut. Ratings 1(poor) to 10(excellent).
[d]Determined according to ASTM D-1646-63 at 280° F. (138C), 5 pt. rise per min.
[e]Si 69, DeGussa, Inc.
[f]A-1100, Union Carbide
[g]A-143, Union Carbide
[h]A-189, Union Carbide

EXAMPLE VII

The rubber composition described in Example VI was again formulated except the coupling agent employed was one of the compounds of the invention, 3-(trimethoxysilyl)propylazide and the corresponding dimer. The results shown in Table III indicate a significant increase in 300% modulus while maintaining about the same tensile strength as compared to the control system without a coupling agent (no. 1, Table II). Heat build-up (ΔT, °C. or hysteresis) is less than the system with no coupling agent which is desirable. Dispersion rate is comparable as well as scorch time. When compared to another system containing a known coupling agent, Si 69 (No. 2, Table II), the inventive azide and dimer has comparable properties. Modulus is slightly lower and hysteresis is slightly higher but elongation is better. Most important, however, is improvement in scorch time. With the inventive azides, the scorch time is comparable to the system without a coupling agent (No. 1, Table II) and 20 to 40% better (higher) than the system with a known coupling agent (No. 2, Table II).

build-up (ΔT) was low. Reducing the concentration of the sulfenamide derivative gives good modulus and tensile strength. The elongation is equal to the control with no coupling agent. Also at the lower concentration, heat build-up is lower and scorch time is close to the control. The lower concentration of the thiosulfenamide derivative also lowers cost. Dispersion appears to be about equal to the control at all concentrations. The principal performance advantage of the thiosulfenamide over the system employing a standard coupling agent (No. 2, Table II) is improved scorch time and elongation.

TABLE IV

Performance Properties of Rubber Compositions Employing Thiosulfenamide-Based Silicon Coupling Agents

| | Coupling Agent | | 300% Modulus$^a$ | | Tensile Strength$^a$ | | % Elongation$^a$ | ΔT, °C.$^a$ | Dispersion Rating$^a$ | Scorch Time$^a$, mins |
|---|---|---|---|---|---|---|---|---|---|---|
| No. | Name | Structure | MPa | psi | MPa | psi | | | | |
| 1. | Control-No Coupling Agent | | 5.48 | 795 | 20.4 | 2954 | 654 | 35.2 | 8 | 17.85 |
| 2. | N,N-Diethyl-3-(trimethoxysilyl)propylthiosulfenamide (1.5 phr) | $(CH_3O)_3Si(CH_2)_3-S-S-N(C_2H_5)_2$ | (b) | (b) | 20.6 | 2988 | 265 | 21.6 | 8 | — |
| 3. | N,N-Diethyl-3-(trimethoxysilyl)propylthiosulfenamide (0.7 phr) | | 10.31 | 1495 | 21.1 | 3062 | 380 | 26.7 | 8 | 12.8 |
| 4. | N,N-Diethyl-3-(trimethoxysilyl)propylthiosulfenamide (0.25 phr) | | 9.02 | 1308 | 26.5 | 3845 | 640 | 32.6 | 7 | 19.3 |

$^a$See footnotes in Table II
(b) Too high to measure

TABLE III

Performance Properties of Rubber Compositions Employing Azide-Based Silicon Coupling Agents

| | Coupling Agent (1.5 phr) | | 300% Modulus$^a$ | | Tensile Strength$^a$ | | % Elongation | ΔT, °C.$^b$ | Dispersion Rating$^c$ | Scorch Time$^d$, mins |
|---|---|---|---|---|---|---|---|---|---|---|
| No. | Name | Structure | MPa | psi | MPa | psi | | | | |
| 1. | Control-No coupling Agent | | 5.48 | 795 | 20.4 | 2954 | 654 | 35.2 | 8 | 17.85 |
| 2. | 3-(Trimethoxysilyl)propylazide | $(CH_3O)_3Si(CH_2)_3-N\overset{N}{\underset{N}{\diagdown\|}}$ | 9.34 | 1355 | 23.1 | 3350 | 557 | 30.6 | 7 | 15.8 |
| 3. | 4.0 wt % 3-(Trimethoxysilyl)propylazide and 61.0 wt % dimer of 3-(Trimethoxysilyl)propylazide | $(CH_3O)_2Si(CH_2)_3-N\overset{N}{\underset{N}{\diagdown\|}}$ <br> $\|$ <br> $O$ <br> $\|$ <br> $(CH_3O)_2Si(CH_2)_3-N\overset{N}{\underset{N}{\diagdown\|}}$ | 11.56 | 1677 | 20.4 | 2963 | 475 | 32.0 | 8 | 19.0 |

$^a$See footnotes in Table II

EXAMPLE VIII

The rubber composition described in Example VI was again formulated except the coupling agent employed was another one of the compounds of the invention, N,N-Diethyl-3-(trimethoxysilyl)propylthiosulfenamide. The results shown in Table IV indicate this compound exhibits outstanding activity as a coupling agent. When used at the same level (1.5 phr) as other coupling agents (Table II), the 300% modulus and tensile strength was too high to measure. At the 1.5 phr level elongation was greatly reduced indicating a highly crosslinked system. In spite of the high activity, the heat

EXAMPLE IX

The rubber composition described in Example VI was again formulated except the coupling agent employed was another one of the compounds of the invention, bis(1-chloro-1-methyl-1-sila-3-cyclopentyl) disulfide and the corresponding monomer 1-chloro-1-methyl-3-mercaptolsilacyclopentane. The results shown in Table V indicate the outstanding properties obtained when the disulfide derivative (No. 3, Table V) of the invention is employed. Modulus is double that of the control system without a coupling agent, tensile strength about 20% higher, elongation about 20% lower but still considered good. The heat build-up (ΔT) is greatly reduced while scorch time is maintained at the same level. The dispersion rate appears about the same. When the monomer is used (No. 2, Table V) physical properties are generally improved. There is an exceptionally low heat build-up but elongation is significantly lowered. When a similar silacyclicmercaptan is employed, 1-ethoxy-1-methyl-3-mercaptosilacyclopentane (No. 4, Table V), performance properties are greatly improved particularly tensile strength. However, scorch time is reduced to an undesirable level.

oxy alkyl silane coupling agents. These materials (Nos. 2 to 6, Table VI) were evaluated to demonstrate the unobviousness of the inventive compounds as silica coupling agents, especially those containing sulfur, by showing that not all thiosilyl compounds are particularly useful as coupling agents. The results shown in Table VI generally indicate these comparative thiosilyls (i.e. dithiocarbamates, thiuram disulfides, trithiocarbonates and benzothiazyl sulfides) give higher tensile strengths but lower 300% modulus. In addition, heat build-up is higher and scorch times are much lower. Also dispersion rates are low indicating poor compati- Employing Thiocyclicsilane-Based Coupling Agents

| No. | Coupling Agent (1.5 phr) Name | Structure | 300% Modulus$^a$ MPa | 300% Modulus$^a$ psi | Tensile Strength$^a$ MPa | Tensile Strength$^a$ psi | % Elongation$^a$ | ΔT, °C.$^a$ | Dispersion Rating$^a$ | Scorch Time$^a$, mins |
|---|---|---|---|---|---|---|---|---|---|---|
| 1. | Control-No Coupling Agent | | 5.48 | 795 | 20.4 | 2954 | 654 | 35.2 | 8 | 17.85 |
| 2. | 1-Chloro-1-methyl-3-mercaptosilacyclopentane | [Cl, CH₃, Si, HS structure] | 15.36 | 2228 | 21.1 | 3060 | 410 | 26.1 | 7 | — |
| 3. | Bis (1-chloro-1-methyl-1-sila-3-cyclopentyl) disulfide | [Cl, CH₃, Si, S]₂ structure | 9.76 | 1416 | 24.2 | 3510 | 542 | 29.8 | 7 | 17.1 |
| 4. | 1-Ethoxy-1-methyl-3-mercaptosila-cyclopentane | [H₅C₂O, CH₃, Si, HS structure] | 12.0 | 1740 | 29.5 | 4279 | 550 | 30.0 | 7 | 2.7 |

$^a$See footnotes in Table II.

bility.

TABLE VI

Performance Properties of Rubber Compositions Employing Sulfur/Silicon-Based Coupling Agents

| No. | Coupling Agent (1.5 phr) Name | Structure | 300% Modulus$^a$ MPa | 300% Modulus$^a$ psi | Tensile Strength$^a$ MPa | Tensile Strength$^a$ psi | % Elongation$^a$ | ΔT, °C.$^a$ | Dispersion Rating$^a$ | Scorch Time$^a$, mins |
|---|---|---|---|---|---|---|---|---|---|---|
| 1. | Control-No Coupling Agent | | 5.48 | 795 | 20.4 | 2954 | 654 | 35.2 | 8 | 17.85 |
| 2. | Sodium N-3-(triethoxysilyl)propyldithiocarbamate | $(C_2H_5O)_3Si(CH_2)_3N(H)-C(=S)-S-Na$ | 5.67 | 822 | 15.8 | 2291 | 447 | 41.0 | 3 | 6.6 |
| 3. | n-Octyl N-3-(triethoxysilyl)propyldithiocarbamate | $(C_2H_5O)_3Si(CH_2)_3N(H)-C(=S)-S-C_8H_{17}$ | 5.50 | 798 | 28.3 | 4105 | 785 | 40.9 | 5 | 7.5 |
| 4. | N-3-(triethoxysilyl)propylthiuram disulfide | $[(C_2H_5O)_3Si(CH_2)_3N(H)-C(=S)-S]_2$ | 5.85 | 849 | 23.3 | 3379 | 680 | 40.0 | 6 | 8.0 |
| 5. | n-Octyl-3-(trimethoxysilyl)propyl trithio carbonate | $(CH_3O)_3Si(CH_2)_3-S-C(=S)-S-C_8H_{17}$ | 8.86 | 1285 | 24.9 | 3611 | 610 | 31.6 | 6 | 13.2 |
| 6. | 3-(Trimethoxysilyl)propylbenzothiazyl-sulfide | $(CH_3O)_3Si(CH_2)_3-S-$(benzothiazyl) | 5.97 | 866 | 22.8 | 3307 | 637 | 28.1 | 8 | — |

$^a$See footnotes in Table II.

EXAMPLE X

The rubber composition described in Example VI was again formulated except the coupling agents employed were various other type sulfur containing alk- Based upon the use of the compounds which follow
1. N,N-Diethyl-3-(trimethoxysilyl)propylthiosulfenamide, 2. 3-(Trimethoxysilyl)propylazide and the dimer,
3. 1-Chloro-1-methyl-3-mercaptosilacyclopentane, and its dimer
4. Bis(1-chloro-1-methyl-1-sila-3 cyclopentyl) disulfide, and
5. 1-ethoxy-1-methyl-3-mercaptosilacyclopentane, The compounds of the invention, when used as coupling agents in silica-filled vulcanizable rubber compositions, generally give at least one and sometimes all of the following advantages over similar type coupling agents and systems without coupling agents:
1. Improved strength (300% modulus, tensile strength)
2. Reduced heat build-up
3. High scorch time.

One skilled in the art in possession of this disclosure, having studied the same can select other compounds, e.g., the dimer of 1-ethoxy-1-methyl-3-mercaptosilacyclopentane to carry out the invention.

Reasonable variation or modification is possible to the foregoing disclosure and the appended claims to the invention, the essence of which is that at least one of an alkoxy alkyl substituted silylazide, an alkoxy alkyl substituted silyl thiosulfenamide, a silacycloalkyl mercaptan and a bis(silacycloalkyl) disulfide is employed as a coupling agent or promoter in a silica-filled rubber.

I claim:
1. A compound suitable for use as a coupling agent in the silica filler reinforcement of a rubber, said compound being represented by one of the formula

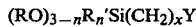

$$(RO)_{3-n}R_n'Si(CH_2)_xY \qquad (I)$$

wherein R and R' are at least one of a linear or branched alkyl or cycloalkyl group having from 1 to 10 carbon atoms or an aromatic or substituted aromatic group having from 6 to 10 carbon atoms, x is an integer from 1 to 20 and Y is one of an azide and a thiosulfenamide, and

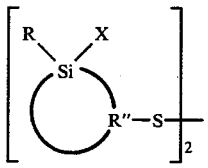

(II)

wherein X is at least one of a halogen and an alkoxy (—OR) group wherein R in said formulas and in said group is as previously defined herein, and R" is a trivalent hydrocarbon radical having 2 to 10 carbon atoms.

2. A compound according to claim 1 wherein the compound is at least one selected from the following:
N,N-Diethyl-3-(trimethoxysilyl)propylthiosulfenamide,
3-(Trimethoxysilyl)propylazide and the dimer, and
Bis(1-chloro-1-methyl-1-sila-3-cyclopentyl) disulfide.
3. A silica reinforced rubber containing a compound according to claim 1.
4. A silica reinforced rubber containing a compound according to claim 2.
5. A method of producing a silica reinforced or filled rubber which comprises employing as a coupling agent at least one compound of claim 1.
6. A method of silica reinforcing a rubber which comprises, employing as coupling agent, a compound of claim 2.
7. A method of producing a silica reinforced rubber which comprises employing one of a compound of Formula I according to claim 1 and such a compound wherein Y is a disubstituted thiosulfenamide, the disubstituted thiosulfenamide group being represented by the formula

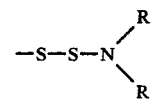

wherein each R can be the same or different as herein defined.
8. A method of producing a silica reinforced rubber which comprises employing as a coupling agent, at least one of
N,N-Diethyl-3-(trimethoxysilyl)propylthiosulfenamide,
3-(Trimethoxysilyl)propylazide and the dimer,
1-Chloro-1-methyl-3-mercaptosilacyclopentane,
Bis(1-chloro-1-methyl-1-sila-3-cyclopentyl) disulfide, and
1-ethoxy-1-methyl-3-mercaptosilacyclopentane.
9. A method, according to claim 5, wherein at least one of the following compounds is employed
trimethoxysilylmethylazide,
2-(trimethoxysilyl)ethylazide,
3-(trimethoxysilyl)propylazide,
4-(trimethoxysilyl)butylazide,
3-(triethoxysilyl)propylazide,
4-(triethoxysilyl)butylazide, and the dimer, trimer, thereof;
N,N-dimethyl(trimethoxysilyl)methylthiosulfenamide,
N,N-dimethyl-2-(trimethoxysilyl)ethylthiosulfenamide,
N,N-dimethyl-3-(trimethoxysilyl)propylthiosulfenamide,
N,N-diethyl-3-(triethoxysilyl)propylthiosulfenamide;
bis(1-chloro-1-methyl-1-sila-3-cyclopentyl) disulfide,
bis(1-chloro-1-ethyl-1-sila-3-cyclopentyl) disulfide,
bis(1-ethoxy-1-methyl-1-sila-3-cyclopentyl) disulfide,
bis(1-ethoxy-1-ethyl-1-sila-3-cyclopentyl) disulfide,
bis(1-chloro-1-methyl-1-sila-3-cyclohexyl) disulfide,
bis(1-chloro-1-methyl-1-sila-4-cyclohexyl) disulfide;
one or more of the coupling agents herein disclosed can be used together.
10. A composition according to claim 8 wherein the rubber is at least one of the following: natural rubber, a homopolymer of a conjugated diene, a copolymer of a conjugated diene and a vinyl aromatic, butyl rubber, and nitrile rubber.
11. A composition according to claim 9 wherein the rubber is at least one of the following: natural rubber, a homopolymer of a conjugated diene, a copolymer of a conjugated diene and a vinyl aromatic, butyl rubber, and nitrile rubber.
12. A silica reinforced rubber having therein at least one compound defined in claim 7.
13. A composition according to claim 12 wherein the rubber is at least one selected from natural rubber, a homopolymer of a conjugated diene, a copolymer of a conjugated diene and a vinyl aromatic, butyl rubber, and nitrile rubber.
14. A composition according to claim 13 wherein the rubber is at least one of a homopolymer of a conjugated diene, and a copolymer of a conjugated diene and a vinyl aromatic.
15. A composition according to claim 14, wherein the conjugated diene is selected from butadiene and isoprene.
16. A composition according to claim 15, wherein the rubber is a styrene-butadiene copolymer rubber (SBR).

* * * * *